US012721869B2

(12) United States Patent
Sanz Herranz et al.

(10) Patent No.: US 12,721,869 B2
(45) Date of Patent: Sep. 1, 2026

(54) ***PHASCOLARCTOBACTERIUM FAECIUM* FOR USE IN THE PREVENTION AND TREATMENT OF OBESITY AND ITS COMORBIDITIES**

(71) Applicant: CONSEJO SUPERIOR DE INVESTIGACIONES CIENTÍFICAS (CSIC), Madrid (ES)

(72) Inventors: Yolanda Sanz Herranz, Paterna (ES); Inmaculada López Almela, Paterna (ES); Eva Mª Gómez Del Pulgar Villanueva, Paterna (ES); Alfonso Benitez-Páez, Paterna (ES); Marina Romani Pérez, Paterna (ES)

(73) Assignee: Consejo Superior de Investigaciones Científicas (CSIC), Madrid (ES)

( * ) Notice: Subject to any disclaimer, the term of this patent is extended or adjusted under 35 U.S.C. 154(b) by 918 days.

(21) Appl. No.: 17/298,377

(22) PCT Filed: Dec. 2, 2019

(86) PCT No.: PCT/ES2019/070821
§ 371 (c)(1),
(2) Date: Aug. 12, 2021

(87) PCT Pub. No.: WO2020/109646
PCT Pub. Date: Jun. 4, 2020

(65) Prior Publication Data

US 2021/0369793 A1 Dec. 2, 2021

(30) Foreign Application Priority Data

Nov. 30, 2018 (ES) ................................ ES201831166

(51) Int. Cl.
*A61K 35/74* (2015.01)
*A23L 33/135* (2016.01)
(Continued)

(52) U.S. Cl.
CPC .......... *A61K 35/741* (2013.01); *A23L 33/135* (2016.08); *C12N 1/205* (2021.05)

(58) Field of Classification Search
CPC ...... A61K 35/741; A23L 33/135; C12N 1/205
See application file for complete search history.

(56) References Cited

U.S. PATENT DOCUMENTS

2013/0224155 A1 8/2013 Kaplan et al.

FOREIGN PATENT DOCUMENTS

JP 2013102714 A * 5/2013
WO 2018117263 A1 6/2018

OTHER PUBLICATIONS

Wu, Feifan, et al. "Phascolarctobacterium faecium abundant colonization in human gastrointestinal tract." Experimental and therapeutic medicine 14.4 (2017): 3122-3126 (Year: 2017).*

(Continued)

*Primary Examiner* — Thane Underdahl
*Assistant Examiner* — Mary A Crum
(74) *Attorney, Agent, or Firm* — Wolf, Greenfield & Sacks, P.C.

(57) ABSTRACT

The present invention relates to the strain *Phascolarctobacterium faecium* DSM 32890 and to its use for the regulation of appetite and the treatment and/or prevention of overweight or the associated metabolic and immunological changes, specifically, hyperglycaemia, glucose intolerance, insulin resistance, dyslipidemia (hypertriglyceridemia, hypercholesterolemia), metabolic syndrome, diabetes and intestinal and/or peripheral tissue inflammation.

4 Claims, 5 Drawing Sheets

Specification includes a Sequence Listing.

(51) Int. Cl.
*A61K 35/741* (2015.01)
*C12N 1/205* (2026.01)

(56) References Cited

OTHER PUBLICATIONS

Han, Hui, et al. "From gut microbiota to host appetite: gut microbiota-derived metabolites as key regulators." Microbiome 9 (2021): 1-16 (Year: 2021).*

Bjerg, Anne Toksvig, et al. "*Lactobacillus paracasei* subsp *paracasei L. casei* W8 suppresses energy intake acutely." Appetite 82 (2014): 111-118 (Year: 2014).*

Tenorio-Jiménez, Carmen, et al. "Effects of probiotics on metabolic syndrome: A systematic review of randomized clinical trials." Nutrients 12.1 (2020): 124 (Year: 2020).*

LPSN Taxonomy, Genus Phascolarctobacterium, 2020 (Year: 2020).*

Appendix A sequence alignment, 2024 (Year: 2024).*

GenBank HQ789471.1, Uncultured organism clone ELU0116-T290-S-NI_000252 small subunit ribosomal RNA gene, partial sequence, 2012 (Year: 2012).*

GenBank LN998073.1, Phascolarctobacterium faecium partial 16S rRNA gene, strain SN20 (Year: 2016).*

Kim, Mincheol, and Jongsik Chun. "16S rRNA gene-based identification of bacteria and archaea using the EzTaxon server." Methods in microbiology. vol. 41. Academic Press, 2014. 61-74 (Year: 2014).*

International Search Report and Written Opinion of the International Searching Authority dated Feb. 7, 2020 for related PCT Application No. PCT/ES2019/070821.

Gibson et al., "Use of a three-stage continuous culture system to study the effect of mucin on dissimilatory sulfate reduction and methanogenesis by mixed populations of human gut bacteria" Applied and Environmental Microbiology, Nov. 1988, vol. 54 No. 11, pp. 2750-2755.

Lesmes et al., "Effects of resistant starch type III polymorphs on human colon microbiota and short chain fatty acids in human gut models" Journal of Agricultural and Food Chemistry, Jun. 11, 2008, vol. 56 No. 13, pp. 5415-5421.

Caramoci et al. "Potential pharmaceutical uses of probiotics and prebiotics in obesity management" Farmacia, Jan. 2017, vol. 65 No. 5, pp. 667-676.

Kobyliak et al., "Probiotics in prevention and treatment of obesity: a critical view" Nutrition & Metabolism, Feb. 20, 2016, vol. 13 No. 14, pp. 1-14.

Muñiz Pedrogo et al., "Gut microbial carbohydrate metabolism hinders weight loss in overweight adults undergoing lifestyle intervention with a volumetric diet" Mayo Clinic Proceedings, Aug. 2018, vol. 93 No. 8, pp. 1104-1110.

Panasevich et al., "Gut microbiota are linked to increased susceptibility to hepatic steatosis in low-aerobic-capacity rats fed an acute high-fat diet" American Journal of Physiology—Gastrointestinal and Liver Physiology, Jun. 10, 2016, vol. 311 No. 1, pp. G166-G179.

Search Report and Written Opinion of the Spanish Patent and Trademark Office dated Mar. 13, 2019 for related Spanish Patent Application No. 201831166.

Del Dot et al., *Phascolarctobacterium faecium* gen. nov, spec. nov., a Novel Taxon of the Sporomusa Group of Bacteria. Systematic and applied microbiology. Nov. 1, 1993;16(3):380-4.

Li et al., Inflammatory bowel diseases phenotype, C. difficile and NOD2 genotype are associated with shifts in human ileum associated microbial composition. PloS one. Jun. 13, 2012;7(6):e26284. 10 pages.

Parker et al., International Code of Nomenclature of Prokaryotes. Prokaryotic Code (2008 Revision). International Journal of Systematic and Evolutionary Microbiology. Jan. 11, 2019;69(1A):S1-S111.

Schober et al., Phascolarctobacterium faecium (DSM 14760, ACM 3679, QUM 3679). BacDive in 2025: the core database for prokaryotic strain data. Creation date 1992. 5 pages. https://doi.org/10.13145/bacdive100.20251217.10 (last accessed Feb. 2, 2026).

* cited by examiner

*PHASCOLARCTOBACTERIUM FAECIUM* FOR USE IN THE PREVENTION AND TREATMENT OF OBESITY AND ITS COMORBIDITIES

CROSS-REFERENCE TO RELATED APPLICATIONS

The present patent application is a U.S. national phase application of International Application No. PCT/ES2019/070821, filed Dec. 2, 2019, which claims priority to Spanish Patent Application No. P201831166, filed Nov. 30, 2018, the disclosures of which are incorporated herein by reference.

INCORPORATION BY REFERENCE

The content of the ASCII text file of the sequence listing named "Sequence_Listing", which is 2,513 bytes in size, was created on and electronically submitted via EFS-Web May 28, 2021, is incorporated by reference herein in its entirety.

The present invention falls within the pharmaceutical and food sectors. Specifically, the present invention relates to the strain with deposit number DSM 32890, the cellular components, metabolites, and secreted molecules thereof, the compositions thereof and/or any of the combinations thereof. It particularly relates to the use of the strain *P. faecium* DSM 32890 for the regulation of appetite and the treatment and/or prevention of overweight and/or obesity, and associated metabolic and immunological changes; specifically, hyperglycaemia, glucose intolerance, insulin resistance, dyslipidemia (hypertriglyceridemia, hypercholesterolemia), metabolic syndrome, diabetes, hepatic steatosis, cardiovascular diseases, and intestinal and/or peripheral tissue inflammation.

BACKGROUND OF THE INVENTION

Obesity constitutes one of the major public health problems due to its high prevalence and comorbidities, which greatly reduce quality of life and increase the risk of death. These comorbidities include, for example, dyslipidemia, metabolic syndrome, diabetes, cardiovascular diseases, atherosclerosis, hepatic steatosis or fatty liver, and hypertension, as well as changes in eating habits.

Obesity occurs as a consequence of a prolonged imbalance between food intake and energy expenditure which leads to weight gain and increased body fat. Energy balance is regulated by neuroendocrine systems controlled in the long and short term. The key hormones in long-term control are insulin and leptin. Insulin is the most important hormone in glucose uptake and in regulating the proper functioning of the adipose tissue and the accumulation of triglycerides. Normal adipose tissue, which is sensitive to insulin, is where fat is stored in response to insulin and other hormones (leptin) by stimulating lipoprotein lipase and inhibiting lipolysis. However, the excessive accumulation of fatty acids in adipose tissue that is associated with obesity reduces insulin sensitivity, which promotes the accumulation of free fatty acids in the form of triglycerides in other organs and tissues (liver, muscle, etc.), and causes changes in production or sensitivity to leptin and the increased synthesis of pro-inflammatory cytokines, which in turn entails a higher risk of developing associated diseases (metabolic syndrome, diabetes, cardiovascular diseases, etc.). Leptin is a hormone/adipokine synthesised mainly by adipose tissue, based on energy reserves and in response to insulin. Leptin regulates energy homeostasis, acting on the level of the central and peripheral nervous system, decreasing energy intake and increasing energy expenditure. Nevertheless, in obese subjects the peripheral concentrations of leptin are abnormally high and resistance to the same and a lack of functionality occurs. The short-term control systems include intestinal hormones which are key to controlling intake at each meal and energy metabolism in different tissues. These hormones are released by enteroendocrine cells (EEC) in response to nutrients and nutrient metabolites, which reach the intestinal lumen where they are detected by specific receptors (for example: G protein-coupled receptors). Among these hormones, it is worth noting cholecystokinin (CCK) secreted by I cells, mainly located in the proximal intestine, and glucagon-like peptide 1 (GLP-1) and peptide YY (PYY) secreted by L cells, mainly present in the distal region of the intestine. Once released, intestinal hormones do not only exert a direct effect on distal organs (liver, white and brown adipose tissue) which enables the control of energy metabolism, but they also act as mediators in the central control of metabolism and eating habits through the neural and endocrine pathways via the gut-brain axis. Among the hormones mentioned, it is worth mentioning GLP-1, which suppresses appetite at the level of the hypothalamus and induces satiety, thus reducing food intake; improves glucose metabolism by inducing insulin secretion in the pancreas and reducing glucagon synthesis; increases energy expenditure; and contributes to the reduction of body weight, hepatic steatosis and the risk of developing diabetes and cardiovascular pathologies. PYY is more stable than GLP-1 and, likewise, acts by inducing satiety and thereby contributes to the reduction of intake and body weight. It also reduces excessive food consumption by activating proopiomelanocortin (POMC) and inhibiting neuropeptide Y (NPY) in the central nervous system. However, excessive consumption of energy-dense foods changes the synthesis of enteroendocrine hormones and the functionality thereof, leading to increased intake and a change in peripheral energy metabolism, aggravating the obesity phenotype.

Obesity is frequently associated with a state of low-grade chronic inflammation involved in metabolic complications, such as type 2 diabetes, cardiovascular diseases and fatty liver. The inflammation of white adipose tissue is considered a causal factor of these metabolic changes and it is characterised by a general increase in pro-inflammatory cells of the immune system such as M1 macrophages (classically activated) and Th1 lymphocytes producing IFNγ, T CD8+ and B cells. On the contrary, a reduction of anti-inflammatory M2 macrophages, Th2 lymphocytes, type 2 innate lymphoid cells (ILC2s) and, frequently, regulatory T cells (Tregs), which would control inflammation, is observed. Adipose tissue has been considered the main contributor to metabolic inflammation and dysfunction in obesity, but now it is known that this phenomenon affects multiple organs, including the brain, muscles, liver, pancreas and the intestine. Most recent evidence suggests that the immune system associated with the intestine and the microorganisms that predominate in the gut, as a result of exposure to unhealthy high-calorie diets, contribute to obesity-associated metabolic inflammation and the intestine may be the origin of metabolic inflammation.

Among the factors involved in obesity, lifestyle changes involving increased intake of energy-dense foods and reduced physical activity and, therefore, reduced energy expenditure are considered the main causes of the obesity epidemic. Preventive and therapeutic strategies based on low-calorie diets and increased physical activity represent the first option in managing obesity and its complications; however, they tend to have limited long-term effectiveness. For this purpose, co-adjuvant alternatives to lifestyle changes are required in order to improve their effectiveness. Moreover, pharmacological strategies, including for example those based on GPL-1 receptor agonists have side effects, partly due to the fact that they are consumed continuously when used to treat chronic pathologies. Furthermore, the effectiveness of pharmacological therapies is limited because they are based on a single therapeutic target, without addressing the complex mechanisms that contribute to obesity and its complications.

Obesity and its comorbidities (type 2 diabetes, dyslipidemia, cardiovascular disease, fatty liver, metabolic syndrome, etc.) have been associated with changes in the composition and functions of the gut microbiota in observational studies in humans, suggesting that gut microbiota could play a significant role in these disorders. This hypothesis has been confirmed by transferring the microbiota of disease or healthy individuals to new subjects and observing that the latter acquired the donor's phenotype. These experiments confirm that the microbiota alterations, partly due to high-caloric diets, contribute to the development of obesity and its metabolic complications. This evidence has led to the development of intervention strategies directed to the intestinal ecosystem, such as the use of probiotics, as an alternative to improve the treatment and prevention of obesity. The products initially developed have been based on bacterial strains belonging to the genera *Lactobacillus* and *Bifidobacterium* due to their history of safe use in food. Nevertheless, it is currently known that other bacteria naturally present in a higher proportion in the human intestine and related to a lean phenotype could be more effective alternatives. Unlike pharmacological strategies, the use of commensal intestinal bacteria would have the advantage of being able to act through various mechanisms of action, regulating both the endocrine and immune systems and, a priori, without causing adverse effects. With regard to the possible beneficial properties of the genus *Phascolarctobacterium*, a published study on rats disclosed that pharmacological treatments used for diabetes (berberine and metformin) modified the microbiota and caused increases in different bacterial groups (*Allobaculum, Bacteroides, Blautia, Butyricicoccus*, and *Phascolarctobacterium*); this led to speculation that this overall modification of the microbiota could be part of the mode of action of anti-diabetic agents, but no direct evidence of this was provided. In a study conducted on rats fed a high-fat diet and subjected to physical exercise or not, the high-fat diet was found to be related to a decrease in the phylum Firmicutes and the low capacity to run with a reduction in *Phascolarctobacterium*; this led to speculation that changes in this microbial group could be partly responsible for the positive effects of physical exercise on the fatty liver; however, no direct evidence of this was given. No previous document demonstrates the beneficial effects of specific species or strains of the genus *Phascolarctobacterium* on the changes and pathologies object of the present invention.

DESCRIPTION OF THE INVENTION

The present invention relates to the strain with deposit number DSM 32890, the cellular components, metabolites, and secreted molecules thereof, the compositions thereof and/or any of the combinations thereof, and to its use for the regulation of appetite and the treatment and/or prevention of overweight and/or obesity, and associated metabolic and immunological changes; specifically, hyperglycaemia, glucose intolerance, insulin resistance, dyslipidemia (hypertriglyceridemia, hypercholesterolemia), metabolic syndrome, type-2 and gestational diabetes, hepatic steatosis and cardiovascular diseases, and also intestinal and/or peripheral tissue inflammation, and associated changes in the gut microbiota.

One of the main beneficial effects of the bacterium object of the patent, as well as of the derivative products, is its capacity to reduce the cellular and humoral mediators of inflammation, associated with obesity and which lead to metabolic dysfunction (for example, insulin resistance, metabolic syndrome and type 2 diabetes).

As described in the examples, in vitro assays (Example 2) demonstrated that the bacterium induces an anti-inflammatory response in peripheral blood mononuclear cells (PBMCs) since it increases the production of anti-inflammatory cytokine IL-4 with respect to pro-inflammatory cytokine IFNγ and decreases the levels of classical monocytes (CD14++CD16−) with respect to the effects induced by lipopolysaccharide LPS, an inducer of inflammation in obesity (Table 1). This anti-inflammatory effect can contribute to improving insulin resistance and glucose intolerance caused by the pro-inflammatory state of obesity to a greater extent than other intestinal bacteria (Example 2).

A fundamental aspect of the invention is the capacity of *P. faecium* to reduce inflammation and protect the intestinal mucosa, reducing the risk of obesity-associated systemic inflammation and in vivo metabolic complications. Specifically, in a diet-induced obesity model (Example 3), *P. faecium* reduces obesity-associated intestinal inflammation, acting both on the innate immune system and on the acquired immune system. For example, this bacterium acts by reducing the population of group 1 innate lymphoid cells (ILC1) in the epithelium, which are increased in obese individuals and promote intestinal inflammation through the production of IFNγ (Example 3; FIG. 4*a*). The production of IFNγ by these cells triggers the polarisation of macrophages towards those of the M1 type (pro-inflammatory phenotype), which are closely involved in obesity-associated inflammation; however, the bacterium is capable of reversing the effect of diet by increasing the levels of M2-type macrophages, thus inducing an anti-inflammatory effect (Example 3; FIG. 4*b*) characterised by the normalisation of the M1/M2 cell ratio (Example 3; FIG. 4*c*) in the lamina propria of the intestine. Furthermore, *P. faecium* reduces obesity-associated inflammatory tone, inducing a Th2-like response and Treg cell production (Example 3; FIGS. 4*d* and 4*e*, respectively). This response has been demonstrated by measuring the levels of Gata3 as a transcription factor mediating a Th2 response and the levels of regulatory T cells with the markers CD25 and FoxP3. The increase in Gata3 also indicates the possible increase in the ILC2 cell population, characterised by producing Th2-type cytokines, which have an anti-inflammatory effect in the context of obesity. The Gata3 transcription factor, in addition to being essential for the development of ILC2s from hematopoietic stem cells (HSC), is also abundant in the subset of mucosal-associated ILC3. The increase in cells of this type (ILC3) in the lamina propria can also contribute to increasing protection of the intestinal mucosa and the barrier function, which is altered in obesity and can contribute to systemic inflammation. *P. faecium* also reduces intraepithelial lymphocyte (IEL) levels and normalises the natural/induced IEL ratio (FIG. 5), altered in obesity. The IELs are located between the epithelial cells of the intestinal tract and, for this reason, they play an essential role in controlling the integrity of the epithelium, and a change of their phenotype can contribute to changes in intestinal permeability and activation of the inflammatory tone characteristic of obesity.

The bacterium object of the patent also has the capacity to modulate the production of gastrointestinal hormones involved in glucose metabolism and in the regulation of appetite, such as GLP-1 and PYY. *P. faecium* restores the expression of PYY and the GLP-1 precursor in the small intestine, which is changed in mice with obesity induced by a high-calorie diet. These hormones are directly responsible for restoring glucose homeostasis and reducing body weight and food intake by facilitating the transmission of satiety signals to brain regions involved in controlling intake, and improving the functioning of peripheral tissues involved in energy metabolism (for example the secretion of insulin in the pancreas and energy expenditure in adipose tissue). These effects would reduce changes in food intake and in lipid and glucose metabolism, which are frequently associated with obesity and which constitute a risk factor that precedes the development of metabolic syndrome, type 2 and gestational diabetes and cardiovascular pathologies.

Therefore, in one aspect, the present invention relates to the strain *P. faecium* with deposit number DSM 32890, hereinafter "strain of the invention" or "strain DSM 32890" or "strain *P. faecium* DSM 32890".

*P. faecium* was isolated from human faeces. The strain was deposited by the Spanish National Research Council (CSIC) on 9 Oct. 2018 under the Budapest Treaty at Deutsche Sammlung von Mikroorganismen und Zellkulture as the International Depository Authority (Leibniz Institute DSMZ-German Collection of Microorganisms and Cell Cultures, Inhoffenstraße 7B, 38124 Braunschweig, GERMANY). The assigned deposit number was DSM 32890.

The scientific classification of the strain of the invention according to the NCBI database is Domain: Bacterium; Phylum: Firmicutes; Class: Negativicutes; Order: Acidaminococcales; Family: Acidaminococcaceae; Genus: *Phascolarctobacterium*; Species: *faecium.*

It is a bacterium found abundantly in the intestinal tract of healthy humans, being a Gram-negative anaerobic bacterium of bacillary morphology that is non-spore-forming and immobile; it usually forms short bacilli, although its size can vary depending on the growth phase and it can lengthen. The colonies are transparent and have an inconsistent texture. It grows at 37° C. under strict anaerobiosis. The bacterium requires succinate, as a carbon source, to grow and produces propionate from this substrate.

Another aspect of the present invention relates to a strain derived from the strain *P. faecium* DSM 32890, wherein said strain maintains or improves the capacities described throughout the present invention. The derived microorganism can be produced naturally or intentionally by mutagenesis methods known in the state of the art such as, but not limited to, the growth of the original microorganism in the presence of mutagenic or stress-causing agents, or by genetic engineering aimed at modifying specific genes. According to a preferred embodiment, the strain derived from the strain *P. faecium* DSM 32890 is a genetically modified mutant. The terms "mutant strain" or "derived strain" can be used interchangeably.

The strain *P. faecium* DSM 32890 or any mutant or derivative thereof can be used in any way that exerts the described effects. According to a preferred embodiment of the present invention, the strain *P. faecium* DSM 32890 is in the form of viable cells (culturable or non-culturable), or according to another preferred embodiment of the invention, the strain is in the form of non-viable cells ("dead" cells inactivated by any technique known in the state of the art such as, but not limited to, heat, freezing or ultraviolet radiation).

Another aspect of the present invention relates to cellular components, metabolites, secreted molecules or any of the combinations thereof, obtained from the strain of the invention, or from a combination of microorganisms comprising at least one strain of the invention.

Cellular components of the bacterium could include components of the cell wall (such as, but not limited to, peptidoglycan), nucleic acids, components of the membrane, or others, such as proteins, lipids and carbohydrates and the combinations thereof, such as lipoproteins, glycolipids or glycoproteins. Metabolites include any molecule produced or modified by the bacterium as a consequence of the metabolic activity thereof during its growth, the use thereof in technological processes (for example, but not limited to, food or drug manufacturing processes), during product storage or during gastrointestinal transit. Examples of these metabolites are, but not limited to, organic and inorganic acids, proteins, peptides, amino acids, enzymes, lipids, carbohydrates, lipoproteins, glycolipids, glycoproteins, vitamins, salts, metals or nucleic acids. Secreted molecules include any molecule exported or released to the outside by the bacterium during its growth, the use thereof in technological processes (for example, food or drug manufacturing), product storage or gastrointestinal transit. Examples of these molecules are, but not limited to, organic and inorganic acids, proteins, peptides, amino acids, enzymes, lipids, carbohydrates, lipoproteins, glycolipids, glycoproteins, vitamins, salts, metals or nucleic acids.

Another aspect of the present invention relates to a composition, hereinafter "composition of the invention", comprising the strain of the invention and/or the cellular components, metabolites, secreted molecules of the strain of the invention or any of the combinations thereof.

The composition, defined in a general way, is a set of components made up of at least the strain of the invention in any concentration; or at least one of the cellular components, metabolites, secreted molecules of the strain of the invention or any of the combinations thereof; or a combination thereof.

In a preferred embodiment, the composition of the invention has a concentration of the strain of the invention of between $10^3$ and $10^{14}$ colony-forming units (cfu) per gram or millilitre of final composition.

In another particular embodiment, the composition of the invention may further comprise at least another additional microorganism different from the strain of the invention and/or the cellular components, metabolites or secreted molecules thereof, or any combination thereof. For example, but not limited to, the additional microorganism that can be part of said composition is selected from at least one of the following groups:

- at least one lactic bacterium or bifidobacterium of intestinal, food or environmental origin. The lactic bacterium is selected from the list consisting of, but not limited to, a bacterium of the genus *Bifidobacterium, Lactobacillus, Lactococcus, Enterococcus, Propionibacterium, Leuconostoc, Weissella, Pediococcus* or *Streptococcus;*
- at least one strain of another species of the genus *Bacteroides* or of the species *Bacteroides uniformis;*
- at least one strain of other phylogenetic groups, genera or species of prokaryotes of intestinal, food or environmental origin, such as, but not limited to, *Archaea, Firmicutes, Bacteroidetes, Proteobacteria, Actinobacteria, Verrucomicrobia, Fusobacteria, Methanobacte-*

*ria, Spirochaetes, Fibrobacteres, Deferribacteres, Deinococcus, Thermus, Cyanobacteria, Methanobrevibacterium, Peptostreptococcus, Ruminococcus, Coprococcus, Subdolingranulum, Dorea, Bulleidia, Anaerofustis, Gemella, Roseburia, Catenibacterium, Dialister, Anaerotruncus, Staphylococcus, Micrococcus, Propionibacterium, Enterobacteriaceae, Faecalibacterium, Bacteroides, Parabacteroides, Prevotella, Eubacterium, Akkermansia, Bacillus, Butyrivibrio, Clostridium* or *Mycobacterium;* at least one strain of fungus or yeast such as, but not limited to, one belonging to the genus *Saccharomyces, Candida, Pichia, Debaryomyces, Torulopsis, Aspergillus, Rhizopus, Mucor* or *Penicillium.*

Said additional microorganism can be a strain of the same species or of a different species or a taxonomic group of microorganisms from the one corresponding to the strain of the invention. The cells comprising the composition may be non-viable or viable and be in any phase of the developmental or growth state (latent, exponential, stationary, etc.), regardless of the morphology it has. In a particular embodiment, said additional microorganism comprises at least one intestinal bacterium or one lactic bacterium.

Optionally, in another particular embodiment, the composition of the invention may further comprise at least one bioactive component (active substance, active ingredient or therapeutic agent), such as other food components, plant products and/or drugs.

The term "bioactive component" refers to a compound with biological activity within the scope of application of the patent which can improve or complement the activity of the strain DSM 32890, including food ingredients or components (for example, but not limited to: polyunsaturated fatty acids, conjugated linoleic acid, prebiotics, fibre, guar gum, glucomannan, chitosan, copper picolinate, calcium, etc.), other probiotics, plants, plant extracts or components and drugs.

In a particular embodiment, the composition of the invention is a pharmaceutical composition. The pharmaceutical composition is a set of components made up of at least the strain of the invention in any concentration; or at least the cellular components, metabolites, secreted molecules of the strain of the invention or any of the combinations thereof, which has at least one application in improving the physical, physiological or psychological well-being of a subject, which implies an improvement in the general state of their health or a reduction in the risk of disease. Said pharmaceutical composition can be a medicament.

The term "medicament" has a more limited meaning than the meaning of "pharmaceutical composition", as defined in the present invention, since "medicament" necessarily implies a preventive or therapeutic effect. The medicament to which the present invention relates may be for human or veterinary use. The "medicament for human use" is any substance or combination of substances that has properties for treating or preventing diseases in humans or that can be used in humans or administered to humans for the purpose of restoring, correcting or modifying physiological functions exerting a pharmacological, immune or metabolic effect, or establishing a medical diagnosis. The "medicament for veterinary use" is any substance or combination of substances that has curative or preventive properties with respect to animal diseases or that can be administered to an animal for the purpose of restoring, correcting or modifying its physiological functions exerting a pharmacological, immune or metabolic effect, or establishing a veterinarian diagnosis. "Veterinary medicaments" will also be considered "premixes for medicated feed" prepared to be incorporated into a feed.

In addition to the requirement of therapeutic efficacy wherein said pharmaceutical composition may require the use of other therapeutic agents, there may be additional fundamental reasons which oblige or recommend to a great extent the use of a combination of a compound of the invention and a bioactive component, wherein said bioactive component is attributed with appropriate activity in order to constitute a medicament. Said compound of the invention obviously refers to the strain of the invention, or the strain derived from it, or the cellular components, metabolites, secreted molecules or any of the combinations thereof, obtained from the strain of the invention.

In a particular embodiment, the pharmaceutical composition further comprises, at least, a pharmacologically acceptable carrier and/or an excipient.

The "carrier" is preferably an inert substance. The function of the carrier is to facilitate the incorporation of other compounds, allow better dosing and administration or give the pharmaceutical composition consistency and shape. Therefore, the carrier is a substance that is used in the medicament to dilute any of the components of the pharmaceutical composition of the present invention to a certain volume or weight; or that, even without diluting said components, is capable of allowing better dosing and administration or giving the medicament consistency and shape. When the form of presentation is liquid, the pharmaceutically acceptable carrier is the diluent.

The term "excipient" refers to a substance that aids the absorption of any of the components of the composition of the present invention, stabilises said components or aids the preparation of the pharmaceutical composition in the sense of giving it consistency or providing flavours that make it more pleasant. Thus, excipients could have the function of holding components together, such as starches, sugars or celluloses, the function of sweetening, the function of colouring, the function of protecting the medicament, for example to isolate it from air and/or moisture, the function of filling a tablet, capsule or any other form of presentation, such as, for example, dibasic calcium phosphate, the function of disintegrating in order to facilitate the dissolution of components and the absorption thereof in the intestine, without excluding other types of excipients not mentioned herein. Therefore, the term "excipient" is defined as a material that, included in galenic forms, is added to active ingredients or to the associations thereof to allow for the preparation and stability thereof, to modify the organoleptic properties thereof or to determine the physicochemical properties of the pharmaceutical composition and the bioavailability thereof. The "pharmaceutically acceptable" excipient must allow for the activity of the compounds of the pharmaceutical composition, in other words, it is compatible with said components.

Furthermore, as understood by a person skilled in the art, the excipient and the carrier must be pharmacologically acceptable, in other words, the excipient and the carrier are allowed and evaluated so that no harm is caused to the organisms to which it is administered.

The pharmaceutical composition or medicament can be presented in any clinically permitted form of administration and in a therapeutically effective amount. For example, it may be in a form adapted for oral, sublingual, nasal, intrathecal, bronchial, lymphatic, rectal, transdermal, inhaled or parenteral administration, preferably in a form adapted for oral administration. The pharmaceutical composition of the invention can be formulated in solid, semi-solid, liquid or gaseous forms, such as a tablet, capsule, powder, granule, ointment, solution, suppository, injection, inhalant, gel, microsphere or aerosol. The form adapted for oral administration is selected from the list comprising, but not limited to, drops, syrup, herbal tea, elixir, suspension, extemporaneous suspension, drinkable vial, tablet, capsule, granulate, sachet, caplet, pellet, pill, lozenge or lyophilised form. In a particular embodiment, the composition of the invention is presented in a form adapted for oral, sublingual, nasal, bronchial, lymphatic, rectal, transdermal, inhaled or parenteral administration.

In a more particular embodiment, the composition of the invention is presented in a form adapted for oral administration. The form adapted for oral administration refers to a physical state that can allow for the oral administration thereof. Said form adapted for oral administration is selected from the list comprising, but not limited to, drops, syrup, herbal tea, elixir, suspension, extemporaneous suspension, drinkable vial, tablet, capsule, granulate, sachet, caplet, pellet, pill, lozenge or lyophilised form.

The "galenic form" or "pharmaceutical form" is the disposition to which the active ingredients and excipients are adapted in order to constitute a medicament. It is defined by the combination of the form in which the pharmaceutical composition is presented by the manufacturer and the form in which it is administered.

In the present invention, the term "therapeutically effective amount" refers to the amount of the component of the pharmaceutical composition that when administered to a mammal, preferably a human, is sufficient to produce prevention and/or treatment, as defined below, of a disease or pathological condition of interest in the mammal, preferably a human. The therapeutically effective amount will vary, for example, according to the activity of the strain of the invention, the cellular components, metabolites, secreted molecules or any of the combinations thereof, in any form of presentation; the therapeutically effective amount will also vary according to the metabolic stability and duration of action of the compound; age, body weight, general state of health, sex and diet of the patient; the mode and time of administration; the excretion rate, the combination of drugs; the seriousness of the particular disorder or pathological condition; and the patient being subjected to therapy, but this can be determined by one skilled in the art according to his or her own knowledge and that description.

Alternatively to the pharmaceutical composition, the composition of the invention can also be a nutritional composition.

The term "nutritional composition" of the present invention refers to a food that, regardless of providing nutrients to the subject who takes it, beneficially affects one or more functions of the body, in a way that provides a better state of health and well-being. Consequently, said nutritional composition can be intended for the prevention and/or treatment of a disease or of the factor causing a disease. Therefore, the term "nutritional composition" of the present invention can be used synonymously with functional food or food for specific nutritional purposes or medicinal food.

In a particular embodiment, the nutritional composition is a food, a supplement, a nutraceutical, a probiotic or a symbiotic.

In a more particular embodiment, the food is selected from the list consisting of a dairy product, a plant product, a meat product, a snack, chocolate, beverage or baby food. The dairy product is selected from the list consisting of a product derived from fermented milk (for example, but not limited to, yoghurt or cheese) or unfermented milk (for example, but not limited to, ice cream, butter, margarine, milk serum). The plant product is, for example, but not limited to, a grain in any form of presentation, fermented or unfermented. The beverage can be, for example, but not limited to, any fruit juice or unfermented milk.

The term "supplement", synonymous with any of the terms "dietary supplement", "nutritional supplement", or "food supplement", is a "food ingredient" intended to supplement food. Some examples of dietary supplements include, but are not limited to, vitamins, minerals, botanicals, amino acids and food components such as enzymes and glandular extracts. They are not presented as substitutes for conventional food or as a sole component of a meal or of the food diet but rather as a complement to the diet.

The term "nutraceutical" as used in the present invention refers to substances isolated from a food and used in a dosage form that have a beneficial effect on health.

The term "probiotic" as used in the present invention refers to live microorganisms that when administered in adequate amounts promote health benefits to the host organism.

The term "synbiotic" as used in the present invention refers to foods that contain a mixture of prebiotics and probiotics. As a general rule, they contain a prebiotic component that favours growth and/or metabolic activity and ultimately the effect of the probiotic with which it is combined, such as, for example and without limitation, the association of fructooligosaccharides or galactooligosaccharides with bifidobacteria.

Another aspect of the present invention relates to the use of the strain of the invention, or the components derived from it, or the composition of the invention, for manufacturing a medicament, a nutritional composition or a food.

Another aspect of the present invention relates to the strain *P. faecium* DSM 32890, a cellular component, metabolite, secreted molecule or any of the combinations thereof obtained from the strain of the invention, or the composition of the invention, for use as a medicament. The term "medicament" has been previously defined, and it is applicable to the present inventive aspect. As explained in previous paragraphs, this medicament can be a pharmaceutical composition or a nutritional composition.

In another aspect, the present invention relates to the strain of the invention, a cellular component, metabolite, secreted molecule or any of the combinations thereof obtained from the strain of the invention, or the composition of the invention, for use in the prevention and/or treatment of overweight and/or obesity, or diseases associated with it.

The term "treatment", as understood in the present invention, refers to combating the effects caused by a disease or pathological condition of interest in a subject (preferably mammal, and more preferably a human) which includes:

(i) inhibiting the disease or pathological condition, in other words, stopping its development;
(ii) alleviating the disease or pathological condition, in other words, causing the remittance of the disease or pathological condition or the symptoms thereof;
(iii) stabilising the disease or pathological condition.

The term "prevention" as understood in the present invention consists of preventing the onset of the disease, in other words, preventing the disease or pathological condition from appearing in a subject (preferably mammal, and more preferably a human), particularly, when said subject has a predisposition for the pathological condition.

The term "overweight" refers to a pathology characterised in that the subject has a body mass index (BMI) equal to or greater than 25. BMI is a measure of association between the weight and height of an individual. To calculate BMI, the following formula is used: the weight of the subject divided by their height squared ($Kg/m^2$). Overweight is characterised by a BMI of between ≥25 to <30. This calculation method is only valid for people over 18 years of age, and as is known by the person skilled in the art, it cannot be applied to minors if a correction factor is not applied. The determination of said correction factor is normal practice for the person skilled in the art.

The term "obesity" refers to a pathology characterised in that the subject has a BMI equal to or greater than 30. Obesity is classified into different levels, considering that subjects with BMI>40 suffer from morbid obesity. Other parameters used to determine whether an individual suffers from central obesity are absolute waist circumference (a male subject is obese when it is >102 cm [central obesity] and a female subject is obese when it is >88 cm) or the waist-to-hip ratio (a male subject is obese when it is >0.9 and a female subject is obese when it is >0.85). An alternative way to determine obesity is to measure the percentage of body fat (a male subject is obese when he has approximately >25% body fat and a female subject is obese when she has approximately >30% body fat).

In the present invention, "diseases associated with overweight and/or obesity" are understood as diseases that are a consequence of the overweight or obesity suffered by the subject. Examples of diseases associated with overweight and/or obesity include, but are not limited to, cardiovascular diseases (such as heart disease, strokes, etc.), metabolic syndrome, diabetes (in particular, type 2 diabetes), hyperglycaemia, insulin resistance, cancer (examples of cancer include, but are not limited to, endometrial, breast, ovary, prostate, liver, gallbladder, kidney and colon cancer), hypertension, dyslipidemia, hypolipidaemia, galactosaemia, phenylketonuria, sitosterolaemia, hyperthyroidism and hypothyroidism.

Thus, in a particular embodiment, diseases associated with overweight and/or obesity are selected from the list consisting of cardiovascular diseases, metabolic syndrome, diabetes, hyperglycaemia, insulin resistance, cancer, hypertension, dyslipidemia, hypolipidaemia, galactosaemia, phenylketonuria, sitosterolaemia, hyperthyroidism and hypothyroidism.

In the present invention, the term "cardiovascular diseases" or "heart disease" refers to diseases that affect the heart and blood vessels including, but not limited to, atherosclerosis, aneurysm, angina, stroke, cerebrovascular disease, congestive heart failure, coronary artery disease, acute myocardial infarction and peripheral vascular disease.

In the present invention, the term "metabolic syndrome" refers to the disease comprising a group of conditions that put the individual at risk of developing heart disease and type 2 diabetes. Examples of these conditions include, but are not limited to, arterial hypertension, high blood glucose, high triglyceride blood levels, low blood levels of HDL and excess fat around the waist. Chronic inflammation and changes in lipid metabolism (dyslipidemia) and glucose are risk factors for cardiovascular pathologies and, therefore, the treatment and prevention thereof can prevent the development of this other group of pathologies.

In the present invention, "diabetes" is understood as a disease characterised by having high blood glucose levels due to the fact that the body does not produce insulin or the cells are unable to use insulin. Insulin is a hormone that helps glucose enter cells to provide them with energy. Over time, a high blood glucose level can cause serious problems to the heart, eyes, kidneys, nerves, gums and teeth.

In the present invention, the term "hyperglycaemia" refers to excessive amounts of glucose in the blood. Methods for measuring the amount of glucose in the blood, as well as the value of glucose based on which it is considered that there is an excess of glucose in the blood, are widely known in the state of the art, and its use is routine practice for a person skilled in the art.

In the present invention, "insulin resistance" is understood as the condition in which tissues exhibit a diminished response in order to have circulating glucose given the action of insulin; especially the liver, skeletal muscle, adipose tissue and the brain. This change, together with a deficiency in insulin production by the pancreas, can lead to the development of type 2 diabetes mellitus after some time.

In the present invention, "cancer" is understood as a disease in which there are abnormal cells that multiply uncontrollably and can invade nearby tissues. The term "cancer" includes tumours, which are an abnormal mass of tissue that appears when cells multiply more than they should or are not destroyed at the appropriate time, and they can be classified as benign (they do not invade nearby tissue or spread to other parts of the body) or malignant (they invade nearby tissue and spread to other parts of the body).

In the present invention, "hypertension" is understood as the continuous or sustained increase of blood pressure levels with respect to normal blood pressure (Maximum levels of systolic blood pressure (maximum) are between 120-129 mmHg, and the maximum levels of diastolic blood pressure (minimum) are between 80 and 84 mmHg).

In the present invention, "dyslipidemia" is understood as the increase in plasma concentrations of cholesterol or triglycerides, or the decrease in concentrations of high-density lipoproteins that contribute to the development of atherosclerosis. "Hypolipidaemia" is understood as a decrease in the plasma concentration of lipoproteins and is defined as a concentration of total cholesterol (TC)<120 mg/dl (<3.1 mmol/L) or of cholesterol associated with low-density lipoprotein (LDL)<50 mg/dl (<1.3 mmol/L).

In the present invention, "galactosaemia" is understood as a hereditary disease characterised in that the individual is unable to use simple sugar galactose, which causes an accumulation thereof within the body, producing lesions in the liver and central nervous system.

In the present invention, "phenylketonuria", also known as PKU, is understood as the congenital change in metabolism caused by the lack of the phenylalanine hydroxylase enzyme, which results in the inability to metabolise the amino acid tyrosine from phenylalanine in the liver.

In the present invention, "sitosterolaemia" is understood as a rare autosomal recessive sterol storage disease characterised by the accumulation of phytosterols in the blood and tissues. Clinical manifestations include xanthomas, arthralgia and premature atherosclerosis. Haematological manifestations include haemolytic anaemia with stomatocytosis and macrothrombocytopenia. The disease is caused by homozygous or compound heterozygous mutations in ABCG5 (2p21) and ABCG8 (2p21) genes.

In the present invention, "hyperthyroidism" is understood as a disease in which the thyroid gland produces too much thyroid hormone, whereas "hypothyroidism" is understood as a disease in which the thyroid gland does not produce enough thyroid hormone to meet the body's needs.

In another aspect, the present invention relates to the non-therapeutic use of the strain of the invention, a cellular component, metabolite, secreted molecule or any of the combinations thereof obtained from the strain of the invention, or the composition of the invention, for the regulation of appetite and/or food intake.

Throughout the description and the claims, the word "comprises" and its variants do not intend to exclude other technical features, additives, components or steps. For those skilled in the art, other objects, advantages and features of the invention may be partially deduced from both the description and the embodiment of the invention. The following examples and figures are provided by way of illustration, and are not intended to limit the present invention.

EXAMPLES

Figure 1:
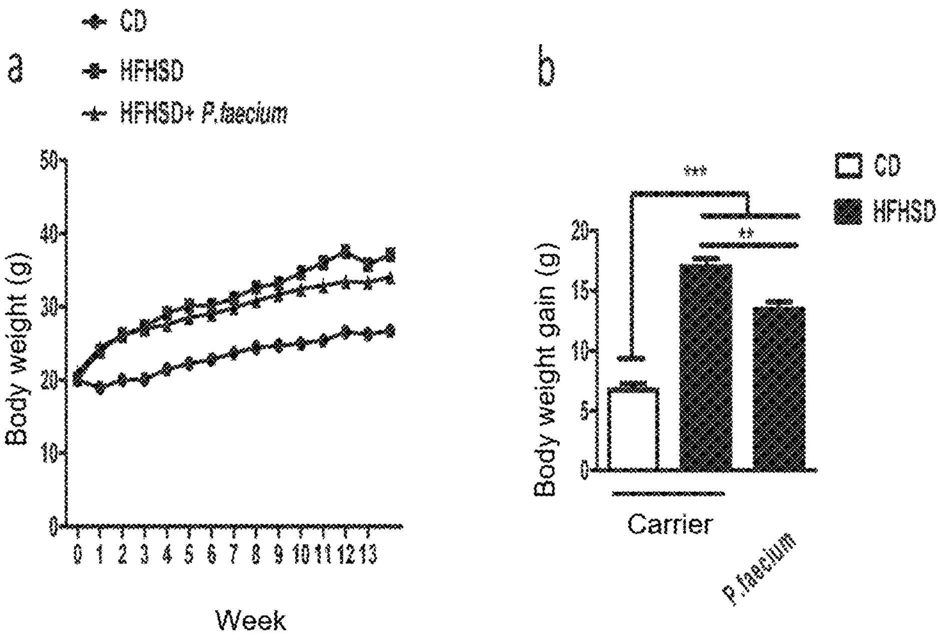
FIG. 1. Effect of administering the strain *P. faecium* ($1\times10^{7-8}$ cfu/day) to C57BL/6 obese mice (n=10/group) for 14 weeks on body weight gain. (a) Weekly body weight. (b) Body weight gain after 14 weeks of treatment. The data are expressed in grams with means and standard error. Statistically significant differences were established by applying one-way ANOVA followed by the Tukey test ($p<0.05$). CD, control diet; HFHSD, high-fat high-sucrose diet; HFHSD+*P. faecium*, high-fat high-sucrose diet+*P. faecium*.

Example 1. Isolation and Identification of the Bacterial Strain *P. Faecium G*104 (*P. Faecium* DSM 32890)

Different intestinal bacteria were isolated from faeces from healthy volunteers. 1.25 grams of faeces were used and diluted in 10 mM phosphate buffer with 0.05% cysteine (1:10 dilution) containing a NaCl concentration of 130 mM (PBS) and homogenised in a Lab-Blender Stomacher 400 (Seward Medical, London, 35 UK). Said dilution was inoculated in 37.5 mL of Intestinal Bacteria Medium (IBM), the composition of which is based on the media recommended in previous publications (Gibson, G. R., et al., Appl. Environ. Microbiol., 54 (1 1): 2750-5, 1988; Lesmes, U et al., J. Agric. Food Chem., 56: 5415-5421, 2008), with some modifications designed by the inventors:

- Main ingredients: distilled water (1,600 mL), peptone water (4 g), $NaHCO_3$ (4 g), $CaCl_2$ (0.02 g), pectin (4 g), xylan (4 g), wheat bran extract (4 g), arabinogalactans (2 g), gum arabic (2 g), starch (10 g), casein (6 g), inulin (2 g) and NaCl (0.2 g). Autoclaved at 121° C. for 60 minutes and left to cool overnight.
- Mucin solution: Mucin (8 g) and distilled water (200 mL). Autoclaved 20 minutes.
- Salts and vitamins: Distilled water (100 mL), $K_2HPO_4$ (0.08 g), $KH_2PO_4$ (0.08 g), $MgSO_4$ (0.02 g), hemin (0.01 g) and menadione (0.002 g)
- Cysteine solution: L-cysteine-HCl (1 g), distilled water (100 mL)

The mixture of salts and vitamins and the cysteine solution were combined and 6M KOH was added until the final solution turned translucent brown and was sterilised by filtration. The final IBM was obtained by mixing the main ingredients, the mucin solution, salts and vitamins and the cysteine solution, making up a volume of 2 L under sterile conditions.

The 50 mL of faeces diluted in IBM medium were fermented for 24 hours in an anaerobic chamber (Whitley DG250 Workstation, Don Whitley Scientific) under stirring and keeping the pH between 6.9-7.0. The IBM medium fermented for 24 hours was filtered (pore size 0.22 μm) and used as a supplement to Fastidious Anaerobe Agar (FAA) medium agar plates with 0.5% defibrinated blood, in which serial dilutions of the fermented faeces were inoculated (0.1 mL of inoculum of each serial dilution in each plate). This supplement of the fermented IBM medium contains substrates produced by gut microbiota, being a medium enriched with nutrients present in the intestinal ecosystem which allows for a better recovery of autochthonous bacteria under laboratory conditions. The inoculated plates were incubated 72 hours at 37° C. in an anaerobic chamber.

Among the colonies that grew after 72 hours on the plate, *Phascolarctobacterium faecium* DSM 32890 was isolated. It was identified by sequencing the 16S rRNA gene (1.26 Kb) using the primers 27f (5'-AGAGTTTGATCCTGGCTCAG-3' (SEQ ID NO: 1)) and 1401r (5'-CGGTGTGTACAA-GACCC-3' (SEQ ID NO: 2)). The reactions after DNA amplification were purified with the Illustra GFX PCR DNA and Gel Band Purification Kits (GE Healthcare) and sequenced by Sanger technology in an ABI 3730XL sequencer (Stabvida-Caparica-Portugal). By comparing the sequences obtained with the NCBI database and the BLASTn algorithm, the identification of the isolated strain (G104) with the species *Phascolarctobacterium faecium* strain ACM 3679 (partial sequence, 16S ribosomal RNA) was obtained with 99% percent identity. The new strain *Phascolarctobacterium faecium* G104 was deposited in the German Collection of Cell Cultures, corresponding to number DSM 32890.

The 16S sequence used for identifying with the BLASTn algorithm and using the oligos 27F and 1401 r for sequencing was the following:

```
>16S G104 partial sequence
                                          (SEQ ID NO: 3)
TCCGACTTCACGCAGGCGGGTTGCAGCCTGCGATCCGAACTGAGATCGGG

TTTCTGGGGTTTGCTCTGCCTCGCGGCTTCGCTTCCCTCTGTTTCCGACC

ATTGTAGTACGTGTGTAGCCCAAGACATAAGGGGCATGATGACTTGACGT

CATCCCCGCCTTCCTCCAGGTTGTCCCTGGCAGTCTCCCATGAGTCCCCA

ACTTTACTTGCTGGTAACATAGGATAGGGGTTGCGCTCGTTGCGGGACTT

AACCCAACATCTCACGACACGAGCTGACGACAGCCATGCACCACCTGTTT

TCTTGTCCCCGAAGGGAAATCTCTATCTCTAGAGCGTTCAATCAATGTCA

AGCCTTGGTAAGGTTCTTCGCGTTGCGTCGAATTAAACCACATACTCCAC

CGCTTGTGCGGGCCCCCGTCAATTCCTTTGAGTTTCAACCTTGCGGCCGT

ACTCCCCAGGCGGGGTACTTATTGCGTTAACTCCGGCACAGAAGGGGTCG

ATACCTCCTACACCTAGTACCCATCGTTTACGGCCAGGACTACCGGGGTA

TCTAATCCCGTTCGCTACCCTGGCTTTCGCATCTCAGCGTCAGACACAGT

CCAGAAAGGCGCCTTCGCCACTGGTGTTCCTCCCAATATCTACGCATTTC

ACCGCTACACTGGGAATTCCCCTTTCCTCTCCTGCACTCAAGCCTAACAG

TTTCCAGCGCCATACGGGGTTGAGCCCCGCATTTTCACGCTCGACTTATT

AAGCCGCCTACATGCTCTTTACGCCCAATAATTCCGGACAACGCTCGCCA

CCTACGTATTACCGCGGCTGCTGGCACGTAGTTAGCCGTGGCTTCCTCGT

TTACTACCGTCATTGCAATGCATTGTTCACACACTGCACGTTCGTCATAA

ACAACAGAGCTTTACAGACCGAAATCCTTCATCACTCACGCGGCGTTGCT

CCGTCAGACTTTCGTCCATTGCGGAAGATTCCCCACTGCTGCCTCCCGTA

GGAGTTTGGGCCGTGTCTCAGTCCCAATGTGGCCGTTCATCCTCTCAGAC

CGGCTACTGATCATCGCCTTGGTAGTCCGTTACACTACCAACTAGCTAAT

CAGACGCAGGCCCATCCTTTAGCGATAGCTTACTTGTAGAGGCCATCTTT

CTTCATCCTGCCATGCGGCACGATGATCACATCCGGTATTAGCACTCCTT

TCGGAATGTTGTCCCCGTCTAAAGGGCAGGTTGCCTACGCGTTACTCACC

CGTTCGCCACTAAGAATTCTACCGAAATAA
```

The specific growth of this strain was optimised for future assays using the medium recommended by the DSMZ culture collection (Medium No. 104b (PY+8 g/l succinate)).

For 1 L of medium, 5.0 g trypticase peptone, 5.0 g meat extract, 10.0 g yeast extract, 2.00 g $K_2HPO_4$, 1.00 mL Tween 80, 40.0 mL salt solution (see below), 1 mg resazurin solution, 0.5 g L-Cysteine-HCl×$H_2O$, 8.0 g sodium succinate, 950.0 mL distilled water, 10.00 mL hemin solution (see below) and 0.20 mL vitamin $K_1$ solution (see below) were mixed.

Salt solution: 0.25 g $CaCl_2$)×2$H_2O$, 0.50 g $MgSO_4$×7 $H_2O$, 1.00 g $K_2HPO_4$, 1.00 g $KH_2PO_4$, 10.00 g $NaHCO_3$, 2.00 g NaCl and 1000.00 mL distilled water.

Hemin solution: Dissolve 50 mg of hemin in 1 mL of 1 N NaOH; bring it to 100 mL with distilled water. Keep refrigerated.

Vitamin K1 solution: Dissolve 0.1 mL of vitamin K1 in 20 mL of 95% ethanol and sterilise by filtration. Store refrigerated and protected from light.

The ingredients were dissolved (except for cysteine, hemin and vitamin K1) and autoclaved for 20 minutes at 121° C. It was left to cool and cysteine, vitamin K1 and hemin were added later. The pH was adjusted to 7.2 and the medium was introduced into an anaerobic chamber to guarantee the anoxic state thereof prior to inoculation of *P. faecium* G104.

Example 2. Selection of *P. Faecium* Based on its Capacity to In Vitro Modulate Inflammation In vitro assays were conducted to comparatively evaluate the immunomodulatory properties of bacteria of human intestinal origin and select the strain capable of inducing the greatest anti-inflammatory response in classical monocytes and therefore with potential therapeutic interest in the treatment of obesity-associated inflammation. To this end, cell suspensions of different bacterial strains were used as a stimulus in cultures of peripheral blood mononuclear cells (PBMCs) and the number of classical monocytes and the levels of the anti-inflammatory cytokine IL-4 with respect to the pro-inflammatory cytokine IFNγ were measured by flow cytometry.

Cultivation and Stimulation of PBMCs.

From whole blood of healthy volunteers, Peripheral Blood Mononuclear Cells (PBMCs) were isolated using a Ficoll gradient (Ficoll Paque-Plus 17-1440-02, Bioscience). After treating them with a solution to lyse erythrocytes (Lysis Buffer for Red Blood Cells, RBC, Miltenyi Biotec., Spain), they were resuspended in RPMI 1640 medium (Gibco, Barcelona, Spain) supplemented with 10% foetal bovine serum (Gibco, Barcelona, Spain), streptomycin (100 μg/mL, Sigma), penicillin (100 U/mL, Sigma) and L-glutamine (Sigma). To perform the experiments, the PBMCs were incubated at a concentration of $10^6$ per mL in 24-well flat-bottom polystyrene plates (Corning, Madrid, Spain) at 37° C., at 5% $CO_2$. Suspensions of live bacteria were used as a stimulus at a concentration of $10^7$ cfu/mL. Purified lipopolysaccharide (LPS) from *Salmonella enterica* serotype *Typhimurium* (Sigma Chemical Co, Madrid, Spain) was used as a positive control at a concentration of 1 μg/mL and untreated PBMC samples were used as negative control. The stimulation time was 24 hours at 37° C., at 5% $CO_2$. After this time elapsed, the cells were collected and centrifuged, separating the cell pellet from the supernatant. Each type of stimulus was assayed in triplicate in 3 independent experiments. The culture supernatants were fractionated and stored in aliquots at −80° C.

Characterisation of the Immunomodulatory Properties of Bacterial Strains on PBMCs by Flow Cytometry.

The stimulated PBMCs were analysed by flow cytometry in order to determine the levels of classical pro-inflammatory monocytes, using the markers CD14 and CD16. Furthermore, pro-inflammatory cytokine IFNγ levels and anti-inflammatory cytokine IL-4 levels in monocytes were evaluated. To this end, the cells were permeabilised and fixed (Fixation/Permeabilization Solution Kit, BD-Bioscience) and resuspended with the FACS solution (PBS1×+BSA 0.2%). Marker levels were measured using BD LSR-Fortessa.

The comparative evaluation of the different bacterial strains made it possible to conclude that the strain of the invention *Phascolarctobacterium faecium* DSM 32890 was the one that induced the most significant immunomodulatory effects, showing a higher production of the anti-inflammatory cytokine IL-4 with respect to the pro-inflammatory IFNγ (higher IL-4/IFNγ) and a reduction of classical monocytes ($CD14^{++}$ $CD16^{-}$) with respect to untreated and LPS-treated cells, which is an inducer of obesity-associated inflammation and its complications (Table 1).

TABLE 1

In vitro characterisation of the immunomodulatory properties of human intestinal bacteria on PBMCs.

| Bacterial strains | Classical Monocytes | IL-4/IFNγ |
|---|---|---|
| Untreated | 0.71 (0.02)b | 1.74 (0.24)d |
| LPS | 1.00 (0.05)a | 0.80 (0.05)e |
| *Alistipes indistinctus* | 0.69 (0.03)b | 3.73 (0.26)b |
| *Phascolarctobacterium faecium* | 0.48 (0.04)c | 4.79 (0.08)a |
| *Bacteroides dorei* | 0.70 (0.06)b | 3.55 (0.20)b |
| *Eubacterium cylindroides* | 0.75 (0.04)b | 1.61 (0.10)d |
| *Eubacterium limosum* | 0.93 (0.03)a | 1.39 (0.07)d |

The results are expressed as the mean and standard error thereof of the relative levels of classical monocytes and the IL-4/IFNγ ratio measured by flow cytometry. Significant differences ($P<0.05$) between groups were established by one-way ANOVA followed by the Tukey post-hoc test. Different letters indicate significant differences between experimental groups ($p<0.05$).

Example 3. Effects of *P. Faecium* in an Animal Model of Obesity

Development of the Animal Model of Obesity and Sampling.

Adult male C57BL/6 mice (6-8 weeks, Charles River, Les Oncins, France), kept under controlled temperature (23° C.), relative humidity (40-50%) and 12-hour light/dark cycle conditions, were fed a high-fat (45% Kcal) high-sugar (sucrose) (17% Kcal) high-calorie diet (HFHSD; D12451, Research diet, Brogaarden, Denmark) or a control diet (CD, 10% Kcal from fat, without sucrose; D12450K, Research diet, Brogaarden, Denmark) for 14 weeks. Daily, the mice fed the HFHSD diet received an oral dose of the bacterial strain object of the invention [($1\times10^{7}$-$1\times10^{-8}$) colony-forming units (CFU)] dissolved in 10% skim milk. The carrier (10% skim milk) was administered in the same way to both the control group with the obese phenotype (HFHSD) and the control group with the lean phenotype (CD) (n=10 mice per group). After 14 weeks, the mice were slaughtered by cervical dislocation in order to obtain samples, including blood, intestine, liver, brain, inguinal and epididymal white adipose tissue, brown adipose tissue, faecal content and faeces.

Characterisation of the Metabolic Phenotype

Body weight was monitored weekly. Fasting basal blood glucose (week 8 and 10) was determined from blood from the saphenous vein using glucose test strips (Contour XT Bayer, Barcelona, Spain) as well as oral glucose tolerance using an oral glucose test (OGTT, week 10) in which glycaemia was measured at 15, 30, 60 and 120 minutes after having administered an oral glucose overload (2 g/Kg) to mice subjected to 4 hours of fasting.

Figure 2:
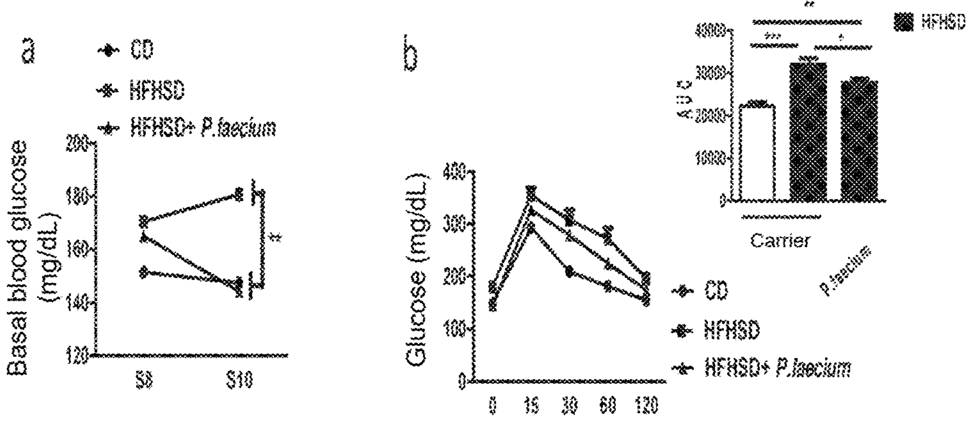
FIG. 2. Effect of administering the strain *P. faecium* ($1\times10^{7-8}$ cfu/day) to C57BL/6 obese mice (n=10/group) for 14 weeks on basal blood glucose and glucose tolerance. (a) Fasting blood glucose levels (mg/dl) at week 8 and 10. (b) Glucose tolerance test, glycaemia was measured at 15, 30, 60 and 120 minutes after having administered an oral glucose overload (2 g/Kg). The Area Under the Curve (AUC) for the glucose tolerance test results is shown. The data are represented with means and standard error. Statistically significant differences were established by applying one-way ANOVA followed by the Tukey test ($p<0.05$). CD, control diet; HFHSD, high-fat high-sucrose diet; HFHSD+*P. faecium*, high-fat high-sucrose diet+*P. faecium*.
Figure 3:
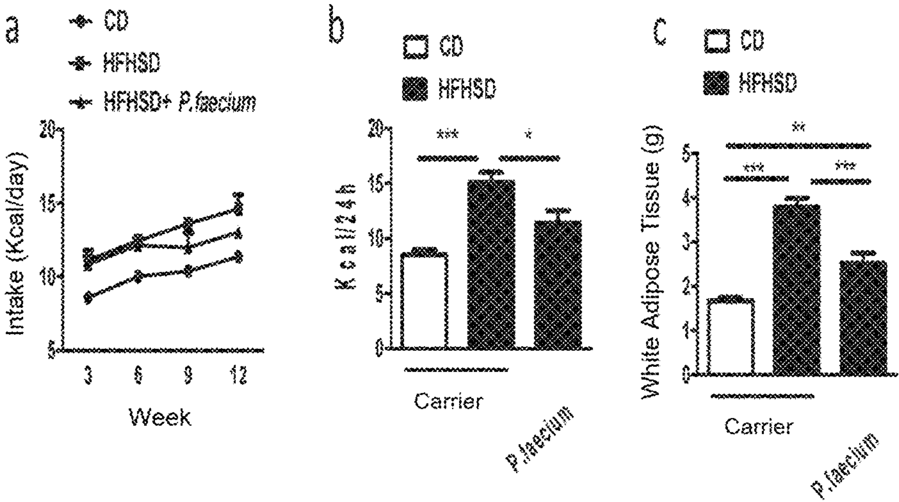
FIG. 3. Effect of administering the strain *P. faecium* ($1\times10^{7-8}$ cfu/day) to C57BL/6 obese mice (n=10/group) for 14 weeks on intake. (a) Relative intake (kcal/day) per animal in weeks 3, 6, 9 and 12. (b) Daily intake (kcal) per animal at week 12 of treatment. (c) Size of white adipose tissue (grams). The data are represented with means and standard error. Statistically significant differences were established by applying one-way ANOVA followed by the Tukey test ($p<0.05$). CD, control diet; HFHSD, high-fat high-sucrose diet.

The bacterium object of intervention reduced weight gain in the diet-induced obesity model (FIGS. 1*a* and 1*b*), as well as adiposity in obese mice after 14 weeks of treatment (FIG. 3*c*). Furthermore, this bacterium improved both basal blood glucose (FIG. 2*a*) and oral glucose tolerance (FIG. 2*b*).

Effects on Intake

The intake recorded weekly in the different cages (5 animals per cage) allowed us to estimate each animal's food intake in kilocalories per day (FIG. 3*a*). The differences observed were confirmed by evaluating individual intake for 24 hours in week 12 of the experiment. The observed result was a reduction in the amount of kilocalories consumed by the group of animals to which the bacterium had been administered, as compared to the obese group (FIG. 3*b*). The regulation of appetite appears to be one of the mechanisms by which the bacterium under study reduces weight and body fat.

Effects on Inflammation

The effects of *P. faecium* on intestinal inflammation were analysed by flow cytometry. For this, the intestine was subjected to digestion stages together with a mechanical treatment, which enabled the epithelium to be separated from the lamina propria. The clean, cut tissue was incubated under stirring for 30 min at 37° C. with the first pre-digestion solution (5 mM EDTA, 1 mM DTT, 100 μg/mL streptomycin and 100 U/mL penicillin in HBSS [Hank's Balanced Salt Solution]). This process was repeated twice, filtering the tissue with 100 μm filters, thus obtaining the cells of the intestinal epithelium. To obtain the cells of the lamina propria, the remaining tissue was treated with the digestion solution (0.5 mg/mL Collagenase D, 50 U/mL DNase I, 3 mg/mL Dispase II, 100 μg/mL streptomycin and 100 U/mL penicillin in HBSS) under stirring for 30 min at 37° C. The process was repeated twice and filtered using 70 μm filters.

The cell suspensions obtained were treated with antibodies from different extracellular and intracellular markers. Specifically, in the epithelium, type 1 innate lymphoid cells were determined (using the lineage markers, T-bet and IFNγ). In the lamina propria, the population of M1 macrophages (F4/80, CD80 and iNOS), M2 macrophages (F4/80, CD80 and iNOS) and Treg (CD3, CD4, CD8, CD25 and Foxp3) was determined. The cells were diluted in FACS solution (1×PBS with 0.2% BSA) and analysed on a BD LSRFortessa flow cytometer (Becton Dickinson, NJ, USA).

In particular, the levels of innate lymphoid cells (ILC) in the epithelium were analysed. These cells are responsible for protecting epithelial barriers against pathogens and maintaining tissue homeostasis. Nevertheless, group 1 ILCs (ILC1) can promote inflammation in tissue through the production of IFNγ and they are increased in obese mice. The evaluated bacterium was able to reduce the proportion of ILC1, thus reducing the inflammation triggered by these cells (FIG. 4*a*).

The bacterial strain also reduced macrophage polarisation towards an M1 (pro-inflammatory) phenotype that can be induced by an increase in IFNγ production. On the contrary, it increased levels of M2, inducing an anti-inflammatory response (FIG. 4*b*) by normalising the M1/M2 ratio (FIG. 4*c*).

Figure 4:
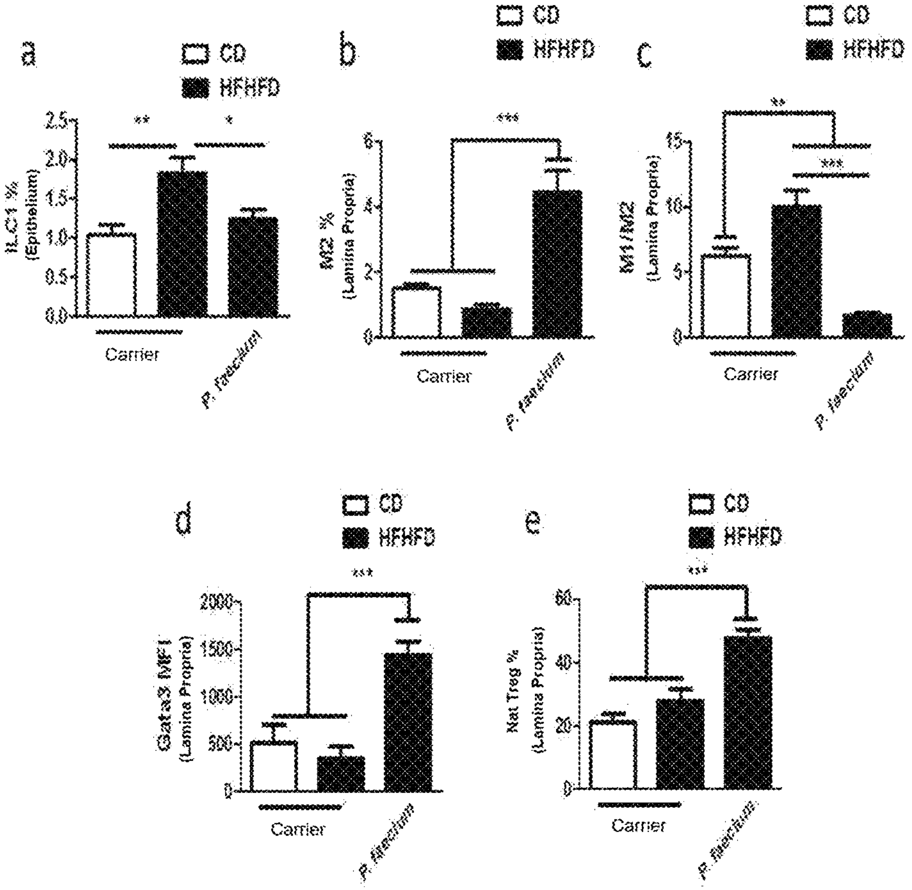
FIG. 4. Effect of administering the strain *P. faecium* ($1\times10^{7-8}$ cfu/day) to C57BL/6 obese mice (n=10/group) for 14 weeks on inflammation. (a) Percentage of ILC1 cells in the epithelium, (b) percentage of macrophages with M2 phenotype (Anti-inflammatory), (c) M1/M2 macrophage ratio (Pro-inflammatory/Anti-inflammatory), (d) Mean fluorescence intensity (MFI) of the Gata3 transcription factor and (e) percentage of regulatory T lymphocytes (Treg). The data are represented with means and standard error. Statistically significant differences were established by applying one-way ANOVA followed by the Tukey test ($p<0.05$). CD, control diet; HFHSD, high-fat high-sucrose diet.

Moreover, *P. faecium* attenuated the effects of obesity by inducing a Th2/Treg-type response (FIGS. 4*d* and 4*e*). This response was evaluated by measuring the levels of Gata3 as a transcription factor mediating a Th2 response and the levels of regulatory T cells with the markers CD25 and FoxP3. The increase in Gata3 could also indicate an increase in the proportion of ILC2 cells and development of ILC3 cells. ILC2 cells are characterised by producing Th2-type cytokines, with an anti-inflammatory effect in the context of obesity. The Gata3 transcription factor has also been described in a subset of intestinal mucosa-associated ILC3 cells that could contribute to the protection thereof.

Figure 5:
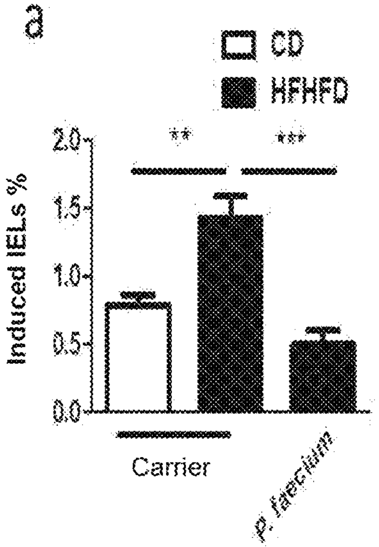
FIG. 5. Effect of administering the strain *P. faecium* ($1\times10^{7-8}$ cfu/day) to C57BL/6 obese mice (n=10/group) for 14 weeks on intraepithelial lymphocytes. (a) Percentage of induced intraepithelial lymphocytes (induced IELs) and (b) natural and induced intraepithelial lymphocyte ratio (nat/ind IEL). The data are represented with means and standard error. Statistically significant differences were established by applying one-way ANOVA followed by the Tukey test ($p<0.05$). CD, control diet; HFHSD, high-fat high-sucrose diet.
Figure 5:
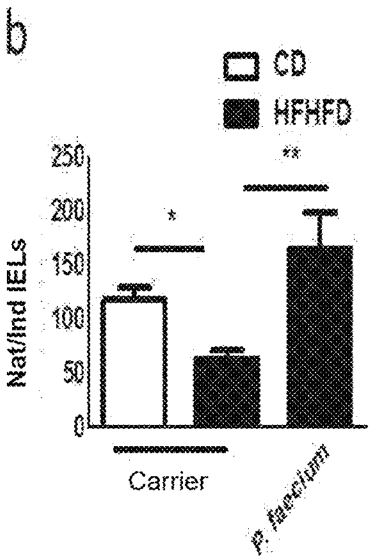

Lastly, *P. faecium* was able to reverse the increase in the proportion of intraepithelial lymphocytes (IEL) induced by the high-calorie diet and normalise the natural/induced IEL ratio (FIG. 5), which would also contribute to re-establishing immune homeostasis and the intestinal barrier, preventing systemic inflammation.

The invention claimed is:

1. A method for the treatment of overweight and/or obesity, or diseases associated with it, comprising administering to a subject in need thereof a strain of *Phascolarctobacterium faecium* with deposit number DSM 32890, wherein diseases associated with overweight and/or obesity are selected from the list consisting of cardiovascular diseases, metabolic syndrome, diabetes, hyperglycaemia, insulin resistance, hypertension, dyslipidemia, and hypothyroidism.

2. A non-therapeutic method for the regulation of appetite comprising administering to a subject in need thereof a strain of *Phascolarctobacterium faecium* with deposit number DSM 32890.

3. The method of claim 1, wherein the strain is administered in an effective amount for the treatment of overweight and/or obesity, or the diseases associated with it, in a composition comprising between $10^3$ and $10^{14}$ colony-forming units (CFU) of the strain per gram or millilitre of the composition.

4. The method of claim 2, wherein the strain is administered in an effective amount for regulation of appetite in the subject, in a composition comprising between $10^3$ and $10^{14}$ colony-forming units (CFU) of the strain per gram or millilitre of the composition.

* * * * *

SEQUENCE LISTING

<160> NUMBER OF SEQ ID NOS: 3

<210> SEQ ID NO 1
<211> LENGTH: 20
<212> TYPE: DNA
<213> ORGANISM: Artificial Sequence
<220> FEATURE:
<223> OTHER INFORMATION: Primer 27f

<400> SEQUENCE: 1
agagtttgat cctggctcag 20

<210> SEQ ID NO 2
<211> LENGTH: 17
<212> TYPE: DNA
<213> ORGANISM: Artificial Sequence
<220> FEATURE:
<223> OTHER INFORMATION: Primer 140r

<400> SEQUENCE: 2
cggtgtgtac aagaccc 17

<210> SEQ ID NO 3
<211> LENGTH: 1280
<212> TYPE: DNA
<213> ORGANISM: Phascolactobacterium faecium

<400> SEQUENCE: 3
tccgacttca cgcaggcggg ttgcagcctg cgatccgaac tgagatcggg tttctggggt 60
ttgctctgcc tcgcggcttc gcttccctct gtttccgacc attgtagtac gtgtgtagcc 120
caagacataa ggggcatgat gacttgacgt catccccgcc ttcctccagg ttgtccctgg 180
cagtctccca tgagtcccca actttacttg ctggtaacat aggatagggg ttgcgctcgt 240
tgcgggactt aacccaacat ctcacgacac gagctgacga cagccatgca ccacctgttt 300
tcttgtcccc gaagggaaat ctctatctct agagcgttca atcaatgtca agccttggta 360
aggttcttcg cgttgcgtcg aattaaacca catactccac cgcttgtgcg ggcccccgtc 420
aattcctttg agtttcaacc ttgcggccgt actccccagg cggggtactt attgcgttaa 480
ctccggcaca gaaggggtcg atacctccta cacctagtac ccatcgttta cggccaggac 540
taccggggta tctaatcccg ttcgctaccc tggctttcgc atctcagcgt cagacacagt 600
ccagaaaggc gccttcgcca ctggtgttcc tcccaatatc tacgcatttc accgctacac 660
tgggaattcc cctttcctct cctgcactca agcctaacag tttccagcgc catacggggt 720
tgagccccgc attttcacgc tcgacttatt aagccgccta catgctcttt acgcccaata 780
attccggaca acgctcgcca cctacgtatt accgcggctg ctggcacgta gttagccgtg 840
gcttcctcgt ttactaccgt cattgcaatg cattgttcac acactgcacg ttcgtcataa 900
acaacagagc tttacagacc gaaatccttc atcactcacg cggcgttgct ccgtcagact 960
ttcgtccatt gcggaagatt ccccactgct gcctcccgta ggagtttggg ccgtgtctca 1020
gtcccaatgt ggccgttcat cctctcagac cggctactga tcatcgcctt ggtagtccgt 1080
tacactacca actagctaat cagacgcagg cccatccttt agcgatagct tacttgtaga 1140
ggccatcttt cttcatcctg ccatgcggca cgatgatcac atccggtatt agcactcctt 1200
tcggaatgtt gtccccgtct aaagggcagg ttgcctacgc gttactcacc cgttcgccac 1260
taagaattct accgaaataa 1280